United States Patent
Rommelaere et al.

(10) Patent No.: US 7,179,456 B2
(45) Date of Patent: Feb. 20, 2007

(54) USE OF PARVOVIRUS FOR BRAIN TUMOR THERAPY

(75) Inventors: Jean Rommelaere, Heidelberg (DE); Jan Cornelis, Neckargemünd (DE); Christiane Dinsart, Ladenburg (DE); Jorg R. Schlehofer, Leimen (DE); Karsten Geletneky, Heidelberg (DE); Marta Herrero Y Calle, Freiburg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 305 days.

(21) Appl. No.: 10/426,709

(22) Filed: Apr. 30, 2003

(65) Prior Publication Data

US 2004/0220124 A1  Nov. 4, 2004

(51) Int. Cl.
*A01N 63/00* (2006.01)
*C12N 15/00* (2006.01)

(52) U.S. Cl. .................. 424/93.1; 435/5; 435/320.1

(58) Field of Classification Search ............... 424/93.1; 435/320.1
See application file for complete search history.

(56) References Cited

OTHER PUBLICATIONS

Fulci et al. Frontiers in Bioscience, 2003, vol. 8, pp. e346-360.*
Telerman et al. Proc. Natl. Acad. Sci. USA, 1993, vol. 90, pp. 8702-8706.*
Oshshima T. et al. J. Gene. Virol. 1998, vol. 79, pp. 3067-3071.*
Lauran Neergaard, "Altered Cold Virus Kills Brain Tumors in Mice," Journal of the National Cancer Institute, May 7, 2003, pp. 1-3.

* cited by examiner

*Primary Examiner*—Bruce R. Campell
*Assistant Examiner*—Bao Qun Li
(74) *Attorney, Agent, or Firm*—Steven J. Hultquist; Intellectual Property/Technology Law

(57) ABSTRACT

Treatment of brain tumors by a composition including parvovirus, e.g., parvovirus H1, LuIII, Mouse minute virus (MMV), Mouse parvovirus (MPV), Rat minute virus (RMV), Rat parvovirus (RPV), Rat virus (RV), vectors based on the foregoing viral species, and/or cells capable of actively producing the foregoing viral species. Also described is the use of a parvovirus for the preparation of a pharmaceutical composition for the treatment of a brain tumor. Tumors for which the compositions and methods of the invention have particular utility include glioma, medulloblastoma and meningioma.

9 Claims, 1 Drawing Sheet

*Figure 1:* *Example of a cranial MRI of succrssful H-1 virus treatment*

MRI imaging before (Fig. 1a)- on day 3 (Fig. 1b) and on day 7 (Fig. 1c) after H-1 virus injection into the tumor. The 3 images in one row show differrent sections of the same examination. The tumor is visible as a white area in the right hemisphere (left half of the scan). The scale on the right is 2 cm.

*Fig 1a:* MRI before *H-1 Virus*
T1-sequence after contrast enhancement

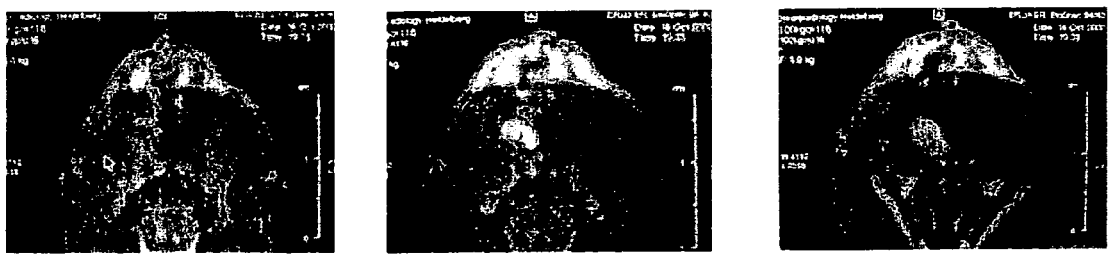

*Fig. 1b:* MRI 3 days after *H-1 virus*
T1-sequence after contrast enhancement

*Fig. 1c:* MRI 7 days after *H-1 virus*
T1-sequence after contrast enhancement

USE OF PARVOVIRUS FOR BRAIN TUMOR THERAPY

BACKGROUND OF THE INVENTION

1. Field of the Invention

The present invention relates to the use of a parvovirus, preferably parvovirus H1 or a related parvovirus such as LuIII, Mouse minute virus (MMV), Mouse parvovirus (MPV), Rat minute virus (RMV), Rat parvovirus (RPV) or Rat virus (RV), or a cell actively producing a parvovirus, for the preparation of pharmaceutical compositions useful for the treatment of brain tumors, such as glioma, medulloblastoma or meningioma. The invention also relates to pharmaceutical compositions for such therapeutic applications, and to corresponding methods of treatment of brain tumors.

2. Description of the Related Art

Malignant human glioblastomas account for the largest number of human malignant brain tumors. The conventional approaches to treatment of gliomas include neurosurgical techniques (resection or stereotactic procedures), radiation therapy and chemotherapy. However, despite these therapies glioblastomas are considered as incurable, since treatment with ionizing radiation, chemotherapy and/or surgical resection achieves only a very limited prolongation of life span of patients. Typically, the average life span after diagnosis is on the order of about 12 to 16 months.

It is accordingly an object of the present invention to provide means and methods of treating brain tumors, e.g., glioma, medullobastoma and meningioma, which overcome the disadvantages of the current therapies and which are fundamentally different from surgical approaches, since even most recent surgical techniques including neuronavigation and intraoperative MRI are not able to significantly improve the therapeutic outcomes for glioblastoma patients.

SUMMARY OF THE INVENTION

The present invention in one aspect relates to a method of treating a brain tumor in a patient, such method comprising administering to the patient an amount of a parvotherapeutic agent that is tumoricidally effective against such brain tumor.

The parvotherapeutic agent comprises parvovirus. Particularly preferred species of parvovirus in the practice of the invention include at least one agent selected from the group consisting of: parvovirus H1, LuIII, Mouse minute virus (MMV), Mouse parvovirus (MPV), Rat minute virus (RMV), Rat parvovirus (RPV), Rat virus (RV), vectors based on the foregoing viral species, and cells capable of actively producing the foregoing viral species.

Another aspect of the invention relates to a pharmaceutical composition useful for treating a brain tumor in a patient, said composition comprising an amount of a parvotherapeutic agent that is tumoricidally effective against said brain tumor, and a pharmaceutically acceptable carrier for said parvotherapeutic agent.

In another aspect, the invention relates to use of a parvovirus or a cell actively producing a parvovirus for the preparation of a pharmaceutical composition for the treatment of a brain tumor.

Other aspects, features and embodiments will be more fully apparent from the ensuing disclosure and appended claims.

BRIEF DESCRIPTION OF THE DRAWINGS

FIG. 1 shows a cranial MRI series for successful H-1 virus treatment of a rat, including MRI imaging before H-1 virus injection into the tumor (FIG. 1a), MRI imaging on day 3 after H-1 virus injection into the tumor (FIG. 1b) and MRI imaging on day 7 after H-1 virus injection into the tumor (FIG. 1c). The three images in each row show different sections of the same examination. The tumor is visible as a white area in the right hemisphere (left half of the scan). The scale on the right is 2 cm.

DETAILED DESCRIPTION OF THE INVENTION, AND PREFERRED EMBODIMENTS THEREOF

The present invention is based on the surprising finding that parvovirus can be successfully used for highly efficient killing of human glioma cells without significantly damaging corresponding normal cells. Autonomous parvoviruses are small single-stranded DNA viruses that rely for their replication on cellular factors expressed during the S-phase of the cell cycle. Parvoviruses are lytic viruses, i.e., they kill infected permissive cells.

In preliminary empirical work associated with the present invention, rat parvovirus H1, which is also infectious for humans, was utilized. By comparing a series of established human tumor cell lines of the same organ origin, it was found that 5 randomly selected human glioma cell lines (U87MG, U373MG, U138MG, U343MG and A172MG) were particularly susceptible to H1 virus infection compared to tumors derived from some other organs (see Table I hereinafter). Cell survival was determined by clonogenicity and vital staining assays.

In addition, 6 different short term/low passage cultures from malignant human brain tumors (5 glioblastomas and 1 gliosarcoma), which had been excised from patients, were propagated in vitro and further characterized by the Department of Neurosurgery at the University of Heidelberg (Germany). These also showed a high rate of susceptibility to H1 infection, similar to the above-mentioned glioma cell lines. The hypersensitivity of human gliomas to H1 virus can be extrapolated to two rat glioma cell lines (RG2 and C6). Likewise, the murine glioma cell line G1261 was very susceptible to the related mouse virus MVMp. These results are consistent with the applicability of mouse and rat glioma cells as appropriate models for the human system.

Parvotherapy according to the present invention is useful for the therapeutic treatment of brain tumors and can significantly improve the prognosis of said tumors. Parvotherapy is usefully employed alone, or alternatively parvotherapy can be utilized in combination with other treatment approaches, e.g., radiation, chemotherapy and/or surgical excision. Parvovirus H1 infection effects killing of tumor cells but does not harm normal brain cells. Parvotherapy can for example be carried out by intracerebral use of a suitable parvovirus, e.g., parvovirus H1, or a related virus or vectors based on such viruses, to effect tumor-specific therapy without adverse neurological or other side effects.

Thus, the present invention contemplates the use of a parvovirus or a cell actively producing a parvovirus for the preparation of a pharmaceutical composition for the treatment of a brain tumor.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for gene therapy, are readily determinable within the skill of the art based on the disclosure herein, without undue empirical effort.

In one preferred embodiment of the present invention, the parvotherapeutic agents are utilized in the treatment of brain tumors such as glioma, medulloblastoma and/or meningioma.

In another preferred embodiment of the invention, the parvotherapeutic agent includes a parvovirus such as parvovirus H1 or a related parvovirus such as LuIII, Mouse minute virus (MMV), Mouse parvovirus (MPV), Rat minute virus (RMV), Rat parvovirus (RPV) or Rat virus (RV).

For administration, the parvotherapeutic agent can be combined with suitable pharmaceutical carriers. Suitable pharmaceutical carriers of a type well known in the art and readily commercially available, include phosphate buffered saline (PBS) solutions, water, emulsions such as oil/water emulsions, wetting agents of various types, sterile solutions, etc. Such carriers can be formulated with the parvotherapeutic agent(s) by conventional formulating methods for administration to the subject at a suitable dose.

Additional pharmaceutically compatible carriers can include gels, biosorbable matrix materials, implantation elements containing the therapeutic agent, or any other suitable vehicle, delivery or dispensing means or material(s).

Patients treatable by the parvotherapeutic treatment methods of the invention include humans as well as non-human animals. Examples of the latter include, without limitation, animals such as cows, sheep, pigs, horses, dogs, and cats.

Administration of the resultant parvotherapeutic pharmaceutical compositions to the brain tumor patient may be effected in any of numerous suitable ways, e.g., by intravenous, intraperetoneal, subcutaneous, intramuscular, topical, intradermal, intracranial, and intratumoral administration. The route of administration, of course, depends on the nature of the brain tumor and the specific therapeutic agent(s) contained in the pharmaceutical composition.

If such parvotherapeutic agent(s) comprise infectious virus particles with the ability to penetrate through the blood-brain barrier, treatment can be performed or at least initiated by intravenous injection of the viral therapeutic agent, e.g., H1 virus.

Since long-term intravenous treatment is susceptible to becoming inefficient as a result of the formation of neutralizing antibodies to the viral therapeutic agent, different modes of administration can be adopted after an initial regimen of intravenous viral administration, or such different administration techniques, e.g., intracranial or intratumoral virus administration, can be alternatively used throughout the entire course of parvoviral treatment.

As another specific administration technique, the parvotherapeutic agent (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus or derived vectors can also be injected into the tumor by stereotactic surgical techniques or by neuronavigation targeting techniques.

Administration of the parvoviral agents or compositions can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvotherapeutic composition is from an implanted article constructed and arranged to dispense the parvotherapeutic agent to the tumoral locus. For example, wafers can be employed that have been impregnated with the parvotherapeutic composition, e.g., parvovirus H1, wherein the wafer is attached to the edges of the resection cavity at the conclusion of surgical tumor removal. Multiple wafers can be employed in such therapeutic intervention.

Cells that actively produce the parvotherapeutic agent, e.g., parvovirus H1, or H1 vectors, can be injected into the tumor, or into the tumoral cavity after tumor removal.

Combinations of two or more of the above-described administration modes can be employed in any suitable manner, e.g., concurrently, contemporaneously, or sequentially.

The dosage regimen of the parvotherapeutic agent is readily determinable within the skill of the art, by the attending physician based on patient data, observations and other clinical factors, including for example the patient's size, body surface area, age, sex, the particular virus, cell, etc. to be administered, the time and route of administration, the tumor type and characteristics, general health of the patient, and other drugs or therapies to which the patient is being subjected.

The features and advantages of the invention will be more fully apparent from the following non-limiting examples.

EXAMPLE 1

Parvovirus H1 Efficiently Kills Rat and Human Glioma Cells in a Dose-dependent Manner Experiments in rats showed that the intracranial injection of $5 \times 10^7$ plaque forming units (pfu) of H1 virus did not induce detectable inflammatory responses. The intracranial implantation of 3000 RG2 tumor cells caused the formation of tumors that were suppressed in a dose-dependent fashion by ex vivo infection of these cells with H1 virus.

Objective: The aim of this study was to evaluate the response of rat and human glioma cells to infection with parvovirus H1 and to assess the use of parvovirus H1 for glioma therapy.

Methods: Rat glioma cell lines C6 and RG2 and the human glioma cell line U343 were infected with different multiplicities of infection (MOI) of purified parvovirus H1. Cell growth of infected cells was compared to growth of uninfected cells by proliferation assay (MTT-test) and by the ability of cells to form colonies after seeding the cells in culture dishes (colony forming assay).

Results: All tested cell lines were successfully infected by H1. MTT tests and colony forming assay (CFA) showed similar results, but effects were more pronounced in the MTT test. RG2 cells were most susceptible to H1. After infection with an MOI of 0.05, approximately 50% of the cells survived, after an MOI of 0.5 only 2% of cells remained alive (CFA). C6 cells showed similar results after MOIs of 1 and 10 (CFA). Human U343 cells reacted similarly to C6 cells. After infection with an MOI of 1, proliferation was reduced to 73%; at MOI 10 only 6.7% of cells survived (MTT). The results are shown in Table I below.

TABLE I

Susceptibility of different brain tumor cells to
parovirus H1 virus-induced killing

|  | Survivals at MOI 5 (%) |
|---|---|
| BRAIN TUMORS | |
| Human glioma cells Cell Lines | |
| A172 | 10[1) |
| U87MG | 0.1[1) |
| U373MG | 2.7[1) |
| U343MG | 18[2) |
| U138MG | <0.1[1) |
| Short term/low passage human glioma cells | |
| NCH37 | 20[2) |
| NCH242 | 13[2) |
| NCH149 | 6[2) |
| NCH89 | 6.9[2) |
| NCH125 | 11.1[2) |
| NCH82 | 2.3[2) |
| Meningeoma primary culture 101202: | Survival MOI 5: 20% |
| Medulloblastoma cell line TE671 | Advanced CPE after H-1 infection in cell culture. |
| Rat glioma cell lines | |
| C6 | 2.4[2) |
| RG2 | <0.1[1) |
| Mouse glioma cell line | |
| GL261 | 0.4[1) |
| OTHER TUMORS | |
| 11 Human Hepatoma cell lines | 17–80 (Refs 1, 2)[1) |
| 3 mammary tumor cell lines | 25–50 (Ref 3)[1) |

Cell survivals were determined by
[1)the capacity of infected cells to form colonies on plastic (clonogenicity assays), or by
[2)the reduction of cell proliferation (MTT-test).
References 1–3 are listed in the Bibliography hereof.

Conclusion: Parvovirus H1 is able to kill rat and human glioma cell lines with high efficacy.

EXAMPLE 2

Intracerebral Injection of Tumorsuppressive Wild-Type Parvovirus H1 does not Cause Damage to Brain Tissue in Immunocompetent Rats Objective: The aim of this investigation was to assess whether or not normal brain tissue exhibits signs of toxic effects after infection with high doses of parvovirus H1, since lack of toxicity is necessary for glioma therapy based on parvovirus H1.

Methods: 8 immunocompetent Wistar rats were stereotactically injected with purified wild type parvovirus H1. After placing a Hamilton needle 4 mm into the right frontal lobe, $1.75 \times 10^7$ particles of H1 virus were slowly applied in a total volume of 5 µl. The animals were killed 7 and 14 days after virus inoculation by lethal injection, and the brains were fixed in 4% paraformaldehyde. Histological examination was performed after HE staining. Cerebrum and cerebellum were evaluated separately since infection with H1 during the fetal period can lead to cerebellar dysplasia in newborn rats.

Results: A total of 16 specimens that had been injected with H1 were examined and compared to 2 specimens after needle placement alone. No brain section showed any signs of inflammatory response or of tissue damage due to cell death after viral infection with H1.

Conclusion: Infection with Parvovirus H1 causes no damage to normal cerebral and cerebellar tissue in adult rats. Since cell killing by H1 only occurred in transformed cells and H1 infection was not harmful for normal-resting cells, H1 infection was validated as a safe methodology for glioma therapy.

EXAMPLE 3

Treatment of Cerebral Tumors with Autonomous Parvoviruses (Parvovirus H-1) in a Rat Model System Animal model: 3000 RG-2 rat glioma cells in 3 µ of DMEM culture medium without supplements were stereotactically injected into the right frontal lobe of the brains of immunocompetent Wistar rats (Charles River, Sulzfeld, Germany) using a stereotactic frame (David Kopf Instruments, Tajunga, Calif., USA). Prior to injection of tumor cells, a 4 mm long 24 gauge Abbocath-T microcatheter (Abbott Ltd., Ireland), was placed into a burr hole that was drilled 1 mm in front of the coronal suture and 2 mm lateral of the midline and further into the right frontal lobe. The injection needle was inserted through the catheter 6 mm deep. The speed of injection was 1 µl of tumor cell suspension per minute using a 10 µl-Hamilton syringe (Hamilton Company, Reno, Nev., U.S.A.). After injection, the needle was withdrawn slowly (1 mm/min) and the catheter was left in place. Tumors developed after 12 to 14 days. Without treatment, the lifespan of tumor-bearing animals was 18 to 21 days.

Magnetic resonance imaging (MRI): Wistar rats were examined in a 2.3 Tesla MRI scanner (Bruker Biospin-MRI GmbH, Tuebingen, Germany) under anaesthesia with ketamine/xylazine. Tumor formation and tumor development after virus injection was monitored after intravenous injection of contrast medium (Omniscan, Amersahm Buchler, Braunschweig, Germany). MRI scans were performed starting at day 14 after injection, every 3 or 4 days, until the animals were dead or the tumor had clearly regressed.

H-1 virus treatment: Tumor-bearing animals were treated on days 16 to 20 after injection of the tumor cells, when the formation of the tumor was demonstrated on MRI scans. The diameters of the treated tumors were between 5 and 8 mm. After reopening of the skin, the injection needle of a 10 µl-Hamilton syringe containing 10 µl of purified H-1 virus (titer: $5 \times 10^9$ plaque forming units (PFU)/cell) was placed into the tumor through the microcatheter. The depth of the needle was determined by the size of the tumor (between 8 and 10 mm). 2 µl of H-1 virus were injected over 2 minutes and after another minute, the needle was retracted 1 mm. Another 2 µl of virus suspension then was injected at the same speed (1 µl/min). This procedure was repeated a total of 5 times, resulting in the administration of 10 µl of H-1 virus into different locations of the tumor. In some additional animals, a second burr hole was drilled 2 mm dorsal of the first burr hole and another 10 µl of H-1 virus were injected with the same technique. In five animals, complete or near-complete regression of intracranial RG-2 gliomas was observed after H-1 virus treatment, including long-term survival for over 4 months in the case of two of the animals. In other animals that were killed 2, 4, 6 days after infection of H-1 virus into the tumor, an increasing level of destruction of tumor cells with time after injection was visible. The sizes of the tumors that were treated in this experiment are properly considered to reflect advanced stages of tumor development, leaving the untreated rats with only 3 to 6 days to live.

A series of MRI images showing the successful treatment of RG-2 glioma is set out in FIG. 1. FIG. 1 shows a cranial MRI series for successful H-1 virus treatment of a rat, including MRI imaging before H-1 virus injection into the tumor (FIG. 1a), MRI imaging on day 3 after H-1 virus injection into the tumor (FIG. 1b) and MRI imaging on day 7 after H-1 virus injection into the tumor (FIG. 1c). The three images in each row show different sections of the same examination. The tumor is visible as a white area in the right hemisphere (left half of the scan). The scale on the right is 2 cm.

The images of FIG. 1 indicate the effectiveness of parvotherapeutic treatment of brain tumors in accordance with the present invention.

Bibliography
1. Moehler M., Blechacz B, Weiskopf N., Zeidler M., Stremmel W., Rommelaere J., Galle P. R., and Cornelis J. J. Effective infection, cell killing and gene transfer of human hepatoma cells but not primary hepatocytes by parvovirus H1. Cancer Gene Ther., 8, 158–167.
2. Guo L. P., Li G. D., Xu H., Huang Q. S., Lin W. M., Ling W. H., Huang H., Luo Z. Y. P53 gene expression of human hepatoma cell lines and their sensitivities to parvovirus H1. Acta Biol. Exp. Sinica 1999, 32, 25–29.
3. Dupressoir T., Vanacker, J-M, Cornelis, J. J., Duponchel N., and Rommelaere J.: Inhibition by parvovirus H-1 of the formation of tumors in nude mice and colonies in vitro by transformed human mammary epithelial cells, Cancer Res 1989, 49, 3203–3208.

While the invention has been described herein with reference to specific features, aspects and embodiments, it will be appreciated that the invention is not thus limited, but rather extends to and includes other features, aspects and embodiments, such as will suggest themselves to those of ordinary skill in the art. Accordingly, the invention is to be broadly interpreted and construed, as regards the spirit and scope of the claims hereafter set forth.

What is claimed is:

1. A method of treating a brain tumor in a patient, said method comprising administering to said patient an amount of parvovirus H1 that is tumoricidally effective against said brain tumor, wherein said parvovirus H1 is administered to the patient by intratumoral administration.

2. The method of claim 1, wherein said brain tumor comprises a tumor selected from the group consisting of glioma, medulloblastoma and meningioma.

3. The method of claim 1, wherein said brain tumor comprises a malignant human glioblastoma.

4. The method of claim 1, wherein said parvovirus H1 is administered to said patient by injection into the brain tumor.

5. The method of claim 4, wherein said injection is carried out during stereotactic surgery.

6. A method of treating a brain tumor in a patient, said method comprising administering to said patient an amount of parvovirus H1 that is tumoricidally effective against said brain tumor, wherein said parvovirus H1 is administered to said patient by injection into the brain tumor and said injection is targeted by neuronavigation.

7. The method of claim 1, wherein said parvovirus H1 is administered to said patient by continuous infusion through an implanted catheter.

8. The method of claim 1, wherein said parvovirus H1 is administered to said patient by implantation in said patient of at least one wafer impregnated with the parvovirus H1.

9. A method of treating a brain tumor in a patient, said method comprising administering to said patient an amount of parvovirus H1 that is tumoricidally effective against said brain tumor, wherein said parvovirus H1 is administered to said patient by implantation in said patient of at least one wafer impregnated with the parvovirus H1, and the implantation comprises implantation in a tumoral cavity formed by surgical removal of tumor tissue.

* * * * *